United States Patent [19]

Green et al.

[11] Patent Number: 4,617,412

[45] Date of Patent: Oct. 14, 1986

[54] TRANSETHERIFICATION PROCESS

[75] Inventors: Michael J. Green, Hull; Gerhard A. Kleiner, London, both of England

[73] Assignee: BP Chemicals Limited, London, England

[21] Appl. No.: 696,031

[22] Filed: Jan. 29, 1985

[30] Foreign Application Priority Data

Feb. 4, 1984 [GB] United Kingdom ................. 8402996
Apr. 5, 1984 [GB] United Kingdom ................. 8408805

[51] Int. Cl.$^4$ ............................ C07F 7/08; C07F 7/18
[52] U.S. Cl. ..................................... 556/446; 556/469
[58] Field of Search ............................... 556/446, 469

[56] References Cited

U.S. PATENT DOCUMENTS

| | | | |
|---|---|---|---|
| 3,133,111 | 5/1964 | Wheeler | 556/446 |
| 3,976,675 | 8/1976 | Scott et al. | 556/446 |
| 4,097,406 | 6/1978 | Scott et al. | 556/446 X |
| 4,172,186 | 10/1979 | Scott et al. | 556/446 X |
| 4,357,473 | 11/1982 | Knollmueller | 556/446 X |

*Primary Examiner*—Paul F. Shaver
*Attorney, Agent, or Firm*—Brooks Haidt Haffner & Delahunty

[57] ABSTRACT

A process for the transetherification of silyl ethers comprises reacting the silyl ether with a hydroxyl containing compound in the presence of a Lewis base containing catalyst. Preferably, the Lewis base containing catalyst is (1) an amidine, (2) a Lewis base in the presence of an epoxide or (3) a trivalent organophosphorus compound in the presence of an activated alkene or alkyne. The Lewis base containing catalyst can either be used in a homogeneous form, soluble in the reactants, or in a heterogeneous form, insoluble in the reactants, having the Lewis base containing catalyst supported on an inert solid. An application of the catalysts is in the production of polydimethylsiloxane polyether block copolymers by reaction of a polydimethylsiloxane silyl ether with a polyether monol.

22 Claims, No Drawings

TRANSETHERIFICATION PROCESS

The present invention relates to a process for the transetherification of silyl ethers.

Chem. Abs. Vol 69 abstract 10503 (1968) discloses a method by which silyl ethers such as $(CH_3)_3SiOC_2H_5$ undergo alcoholysis in the presence of an alcohol and an acid.

Chem. Abs. Vol. 49 abstract 15426 (1955) also discusses a method by which silyl ethers may be transetherified but this method uses an aromatic alcohol only in the presence of sodium metal as catalyst.

It has now been found that the transetherification of silyl ethers can be carried out in the presence of a Lewis base containing catalyst.

Accordingly, the present invention provides a process for the transetherification of silyl ethers characterised in that a silyl ether and a hydroxyl containing compound are reacted together in the presence of a Lewis base containing catalyst.

By the term 'transetherification process' is meant a reaction in which one or more ether groups attached to a molecule are exchanged with an equivalent number of ether groups derived from one or more molecules containing a hydroxyl group. An example of such a transetherification process is $$(CH_3)_3Si(OCH_3) + C_2H_5OH \rightarrow (CH_3)_3Si(OC_2H_5) + CH_3OH$$

During the exchange of ether groups in the transetherification process a molecule containing a hydroxyl group is formed corresponding to the formula of the ether group which has been exchanged. It is not intended in this document to limit the term hydroxyl group to —OH alone. The term also includes groups such as —SH.

The silyl ethers used in the transetherification process may be, for example, of the form $R_xSi(OR^1)_{4-x}$ where x is an integer from 0 to 3 and R and $R^1$ are independently substituted or unsubstituted alkyl, cycloalkyl, aryl, vinyl or allyl hydrocarbyl groups. The R groups which are chemically bonded to the silicon atom directly may be the same or different and R1 may be the same or different to any of the R groups. Alternatively, the silicon atom to which the ether groups are attached may form part of a polymeric oxysilicon compound for example a polysiloxane or silica e.g.

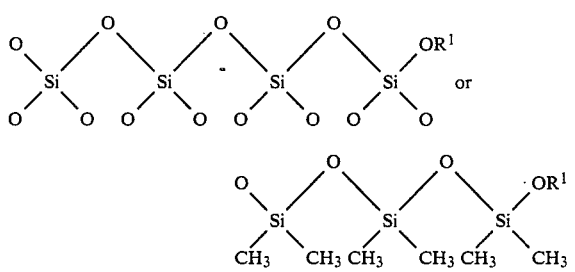

or $(R)_a$—$Si((OSiR^1)_b$—$OR)_{4-a}$ where a = 0–3 and b ≥ 0

The hydroxyl containing compound used may be an aliphatic, cycloaliphatic or aromatic alcohol or a substituted derivative thereof. Unsaturated alcohols e.g. allyl alcohol or polyols e.g. diols and triols may also be used. Preferred alcohols include ethanol, methanol, propanol, phenol, and simple monols, diols and triols such as ethylene glycol and sorbitol. The hydroxyl containing compound may also be a thio alcohol e.g. methane thiol.

Polyether monols or polyol such as those formed by polymerising ethylene oxide and/or propylene oxide on saturated or unsaturated mono- or poly-functional alcohols are also preferred. Such polyether monols or polyols may be either random or block copolymers of ethylene oxide and propylene oxide attached to a simple monol or polyol.

One particular application of the transetherification process described is for the production of polydimethylsiloxane-polyether block copolymers of the general structure $$(CH_3)_ySi((O—Si—(CH_3)_2)_p—O—(C_3H_6O)_n(C_2H_4O)_m—(CH_2)_3CH_3)_{4-y}$$

where
y = 0 to 3
p > 0
m > 0
n > 0
by reaction of $(CH_3)_ySi((O—Si—(CH_3)_2)_p—OCH_2CH_3)_{4-y}$ with a polyether monol such as $CH_3(CH_2)_3—O—(C_2H_4O)_m(C_3H_6O)_n—OH$.

The transetherification of silyl ethers is catalysed by a Lewis base containing catalyst. The term Lewis base is one familiar to the skilled man and is defined, for example, on page 614 of 'The Condensed Chemical Dictionary (10th Edition)' published by Van Nostrand Reinhold Company. Examples of Lewis bases include amines, phosphines, arsines and stibines. Suitably, the Lewis base used in the present invention is a strong base or is capable of generating a strong base in the presence of other catalyst components. Hence the Lewis base containing catalysts used in the present invention are themselves strongly basic.

Preferably, the Lewis base containing catalyst belongs to one or more of the following three classes of compounds;
(1) an amidine,
(2) a Lewis base in the presence of an epoxide, and
(3) a trivalent organophosphorus compound in the presence of an activated alkene or alkyne.

By the term amidine is meant a compound containing the grouping

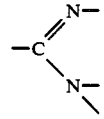

Conveniently the free valencies on the nitrogen atom are attached to carbon atoms or hydrogen and the free valency on the carbon to another carbon or nitrogen atoms. In the last mentioned case the structure comprises a guanidine grouping.

A preferred class of amidines is the cyclic amidines. Cyclic amidines are defined as those amidines wherein at least one of the nitrogen atoms is part of an alicyclic or heterocyclic substituted or unsubstituted hydrocarbyl ring. In the case where the amidine is a guanidine then any two of the three nitrogen atoms may be in the same or different rings. Those nitrogen atoms which are not part of any such ring may form part of a substituted or unsubstituted hydrocarbyl group.

A preferred class of cyclic amidines is that in which the amidine group can form part of a fused ring system containing 6 and 5 membered rings or 6 and 7 membered rings or two six membered rings, as for example in 1,5-diazabicyclo[4.3.0]non-5-ene which has the formula

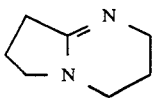

or 1,8-diazabicyclo[5.4.0]undec-7-ene of the formula

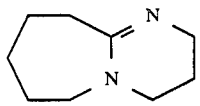

or 1,5,7-triazabicyclo[4.4.0]dec-5-ene of formula

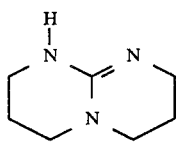

Where the catalyst comprises a Lewis base and an epoxide the epoxide which is used in the presence of the Lewis base is preferably a lower alkylene oxide such as ethylene oxide, propylene oxide or butylene oxide. The ratio of Lewis base to epoxide suitably lies in the range 1:1 to 1:5. In such cases the Lewis base is preferably an amidine or an alkylamine e.g. triethylamine.

Where the catalyst is an organophosphorus containing compound/activated alkene/alkyne catalyst it suitably comprises the following parts
(i) an organophosphorus containing compound in which the phosphorus is trivalent, and
(ii) a compound containing both
  (a) a double or triple bond, and
  (b) an electron withdrawing group
the latter said compound being reactable in the Michael reaction.

The organophosphorus-containing compound can suitably be a mopo-, di- or trialkyl phosphine in which each of the alkyl groups is a $C_1$ to $C_{10}$ alkyl group or a mono-, di or triaryl phosphine such as triphenylphosphine and can contain more than one phosphorus atom e.g. $Ph_2PCH_2CH_2PPh_2$.

The compound (ii) containing the double or triple bond and electron withdrawing group can be of the formula

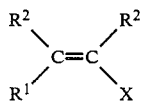

or $R^1$—C≡C—X where X is an electron withdrawing group, for example —COOR, —COR, CHO, $CONH_2$, $CON(R)_2$ or CN, where R is an alkyl or aryl group, and where $R^1$, $R^2$ and $R^3$ are monovalent hydrocarbyl groups or hydrogen.

The molar proportions of the two components of the catalyst system are such as to provide from 10:1 to 1:10, preferably 2:1 to 1:2 atoms of phosphorus per double or triple bond.

Conveniently the catalyst system comprises a solvent in which both components are dissolved. The solvent is suitably an aliphatic alcohol and is preferably selected from the following alcohols, methanol, ethanol, propanol and butanol. The solvent can of course be one of the reactants.

The catalyst system can be prepared by mixing the two components in the presence of the solvent or one or more of the reactants.

For any of the three classes of catalyst, suitable catalyst concentrations are in the range 0.0001 to 1% by weight of the total reaction mixture. Preferably the catalyst concentration lies in the range 0.001% to 1%.

The Lewis base containing catalyst may be supported on an inert solid to render the catalyst insoluble in the reaction mixture. Such heterogeneous Lewis base containing catalysts are more easily separated from the reaction mixture at the end of the reaction than equivalent soluble (homogeneous) versions.

The amidine or guanidines catalysts described above may be supported by chemically or physically bonding the molecule to an inert solid. This can be achieved, for example, by bonding the surface atoms of the solid to one or more of the free valences of the amidine or guanidine group either directly or through an intermediate hydrocarbyl radical. In the case of cyclic amidies or guanidines the hydrocarbyl radical may constitute part of the ring structure of the molecule.

As an aternative to a supported amidine or guanidine catalyst, a supported Lewis base/epoxide catalyst can be used. In such cataysts, it is possible either
(i) to support the Lewis base on the inert solid and have the epoxide component initially present in solution with the reactants.
or
(ii) to support the epoxide on the inert solid and have the Lewis base component initially present in solution with the reactants.

The epoxide component, if initially present in solution is suitably a lower alkylene oxide for example ethylene oxide, propylene oxide and butylene oxide. If the epoxide is supported on the inert solid it also may be bonded to the solid via one or more of the groups attached to the epoxide moiety. However, if the inert solid is an organic resin it is possible to prepare the epoxy modified resin directly by polymerising epoxy functionalised monomers.

The trivalent organophosphorus compound/activated alkene or alkyne catalyst can also be used in a heterogeneous form. In this case either of the two components may be bound to the inert solid with the other component intially present in solution.

The inert soid may be either organic, such as a resin or a polymer, e.g. polystyrene, a polystyrene/divinylbenzene copolymer, a polyacrylate, polypropylene and the like, or inorganic such as a silica, clay, diatomaceous earth, zeolite, alumina or aluminosilicate. Preferred supports are polystyrene and its copolymers with divinylbenzene, copolymers of glycidyl methacrylate and ethyene glycol dimethacrylate and the like.

Examples of the supported strong base catalysts are TBD supported on polystyrene or polystyrene/divinylbenzene copolymer, Amberlite IRA-93, Amberlyst I5 and Duolite A375.

The Lewis base containing catalyst is suitably present on the solid in amounts corresponding to between 0.1 and 10 moles of catalyst per gram of solid.

It is clearly important that the solid is not degraded under the reaction conditions. Hence by the term inert solid is meant a solid which does not undergo physical or chemical degradation during the reaction or subsequent processing. Since the reaction conditions may vary depending upon the nature of the reactants, reaction temperature, reaction time and the nature of any solvent used, the choice of inert solid will therefore reflect the particular needs and constraints of the transetherification process to be operated.

The molar ratio of hydroxyl containing compound to silyl ether should preferably lie in the range 1:10 to 10:1.

It is possible to carry out the transetherification reaction over a range of temperatures but the preferred range is from 0° C. to 100° C.

The reaction may be carried out batchwise or continuously.

The invention will now be illustrated by reference to the following Examples.

EXAMPLES 1-3 and COMPARATIVE TEST A 1 g of trimethylethoxysilane was added to a solution containing 1 g of methanol and the appropriate amount of 1,5,7-triazabicyclo[4.4.0]dec-5-ene (TBD) and the resulting mixture was maintained at 21° C. for 2 hrs. At the end of this time the liquid product was analysed by gas chromatography. The % conversion of trimethylethoxysilane to trimethylmethoxysilane is presented in the table together with the weight of TBD used.

| EXAMPLE OR TEST | WT OF TBD USED (g) | % CONVERSION TO $(CH_3)_3SiOCH_3$ |
| --- | --- | --- |
| 1 | 0.01 | 79 |
| 2 | 0.001 | 80.5 |
| 3 | 0.0001 | 60.4 |
| A | — | <1 |

Test A does not constitute part of the invention as described herein but shows that no reaction occurs in the absence of catalyst.

EXAMPLE 4-6

These examples illustrate the use of other amidine catalysts. The method of Example 1 was followed. The catalyst and the weight used are given in the table together with the % conversion of trimethylethoxysilane to trimethylmethoxysilane.

| EXAMPLE | AMIDINE USED | WT USED | % CONVERSION TO $(CH_3)_3SiOCH_3$ |
| --- | --- | --- | --- |
| 4 | 1,8-diazabicyclo[5.4.0]dec-7-ene | 0.0017 g | 80.2 |
| 5 | 1,5-diazabicyclo[4.3.0]non-5-ene | 0.0009 g | 83.8 |
| 6 | tetramethylguanidine | 0.001 g | 71.1 |

EXAMPLE 7

A solution containing 10 g of methanol, 0.6 g of 1,2 butylene oxide, and 0.75 g of triethylamine was heated to 100° C. in a sealed Fischer-Porter tube under an initial nitrogen pressure of 50 psi. The tube was immediately cooled, depressurised, and the resulting solution diluted 10 fold with methanol, and 1 g of this solution was added to 1 g of trimethylethoxysilane. Analysis of the liquid product after 2 hours showed a trimethylethoxysilane conversion of 79.7% to trimethylmethoxysilane. This example shows that a Lewis base and an epoxide can be used as catalyst for the transetherification reaction.

EXAMPLE 8

Example 7 was repeated except that 0.01 g of tributyl phosphine was used in place of triethylamine and the amount of butylene oxide used was reduced to 0.01 g. Analysis of the liquid product showed a trimethylethoxysilane conversion of 79.9% to trimethylmethoxysilane.

EXAMPLE 9

Example 1 was repeated except that 0.001 g of tributylphosphine and 0.001 g of ethyl acrylate were used in place of TBD. Analysis of the liquid product showed a trimethylethoxysilane conversion of a 86% to trimethylmethoxysilane. This example shows that a phosphine and an activated alkene can be used as a catalyst.

COMPARATIVE TEST B

Example 9 was repeated in the absence of ethyl acrylate. Analysis of the liquid product showed a trimethylethoxysilane conversion of 2% to trimethylmethoxysilane. Test B does not constitute part of this invention but does show that the activated alkene is an essential feature of the catalyst when a phosphine is used.

EXAMPLE 10

Trimethylmethoxysilane (0.5 g) was added to a solution containing 1 g of ethanol and 0.0067 g of TBD. Analysis of the liquid product after 2 hours showed a trimethylmethoxysilane conversion of 80.4% to trimethylethoxysilane.

EXAMPLE 11

Example 7 was repeated in the absence of 1,2-butylene oxide. Analysis of the liquid product showed a trimethylmethoxysilane coversion of 6.7% to trimethylethoxysilane.

EXAMPLE 12

2 g of Duolite A375 (a tertiary amine containing ion exchange resin) was washed with 100 ml of dry methanol and the resulting anhydrous resin refluxed for 1 hour with 10 g of methanol and 0.5 g of 1,2-butylene oxide. The mixture was cooled to room temperature and 10 g of trimethylethoxysiliane added. Analysis of the liquid product after 2 hours showed a trimethylethoxysilane coversion of 78.2% to trimethylmethoxysilane.

We claim:

1. A process for the transetherification of silyl ethers characterised in that a silyl ether and a hydroxyl containing compound are reacted together in the presence of a Lewis base contaiing catalyst,
wherein said catalyst is selected from the group consisting of
    (1) an amidine, or a guanidine,
    (2) a Lewis base in the presence of an epoxide, and
    (3) a trivalent organophosphorus compound in the presence of an activated alkene or alkyne.

2. A process as claimed in claim 1 characterised in that the Lewis base containing catalyst is an amidiine.

3. A process as claimed in claim 2 characterised in that the amidine is a cyclic amidine.

4. A process as claimed in claim 2 characterised in that the amidine is a guanidine.

5. A process as claimed in claim 3 characterised in that the cyclic amidine is a cyclic guanidine.

6. A process as claimed in claim 3 characterised in that the cyclic amidine has an amidine group which forms part of a fused ring system containing 6 and 5 membered rings, or 6 and 7 membered rings or two six membered rings.

7. A process as claimed in claim 6 characterised in that the cyclic amidine is selected from the group comprising 1,5-diazabicyclo[4.3.0]-non-5-ene, 1,8-diazabicyclo[5.4.0]undec-7-ene and 1,5,7-triazabicyclo[4.4.0]dec-5-ene.

8. A process as claimed in claim 1 characterised in that the Lewis base containing catalyst comprises a Lewis base and an epoxide.

9. A process as claimed in claim 8 characterised in that the Lewis base is an amine.

10. A process as claimed in claim 9 characterised in that the amine is an amidine.

11. A process as claimed in claim 8 characterised in that the amine is an alkylamine.

12. A process as claimed in claim 1 characterised in that the Lewis base containing catalyst comprises a trivalent organophosphorus compound in the presence of an activated alkene or alkyne reactable in the Michael reaction.

13. A process as claimed in claim 12 characterised in that the activated alkene or alkyne is of the formula

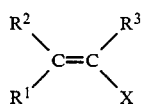

or R$^1$—C≡C—X where X is an electron withdrawing group, and where R$^1$, R$^2$ and R$^3$ are monovalent hydrocarbyl groups or hydrogen, 14. A process as claimed in claim 12 characterised in that the trivalent organophosphorus compound is a mono-, di- or trialkyl phosphine or a mono-, di- or triaryl phosphine.

15. A process as claimed in claim 13 characterised in that X is an electron withdrawing group selected from —COOR, —COR, —CONH$_2$, —CON(R)$_2$ or —CN where R is an alkyl or aryl group.

16. A process as claimed in claim 12 characterised in that the Lewis base catalyst is prepared by dissolving the trivalent organophosphorus compound and the activated alkene or alkyne in a solvent.

17. A process as claimed in claim 1 characterised in that the hydroxyl containing compound is an alcohol.

18. A process as claimed in claim 17 characterised in that the alcohol is selected from the group consisting of ethanol, methanol, propanol, phenol, ethylene glycol and higher molecular weight monols, diols and triols.

19. A process as claimed in claim 17 characterised in that the alcohol is a polyether monol or polyol.

20. A process as claimed in claim 1 characterised in that the silyl ether is of the form R$_x$Si(OR$^1$)$_{4-x}$ where x is an integer from 0 to 3 and R and R1 are independently substituted or unsubstituted alkyl, cycloalkyl, aryl, vinyl or allyl hydrocarbyl radicals.

21. A process as claimed in claim 1 characterised in that the ether is of the formula (CH$_3$)$_y$Si((0—Si—(CH$_3$)2)$_p$—OCH$_2$CH$_3$)$_{4-y}$ and the hydroxyl containing compound is of the formula CH$_3$(CH$_2$)$_3$ —O—(C$_2$H$_4$O)$_m$(C$_3$H$_6$O)$_n$—OH where
y=0 to 3 p0 P>0
m>0
n>0.

22. A process as claimed in claim 1 characterised in that the Lewis base containing catalyst is supported upon an inert solid.

* * * * *

UNITED STATES PATENT AND TRADEMARK OFFICE
CERTIFICATE OF CORRECTION

PATENT NO. : 4,617,412

DATED : October 14, 1986

INVENTOR(S) : Michael J. GREEN et al

It is certified that error appears in the above-identified patent and that said Letters Patent is hereby corrected as shown below:

Col. 1, line 30. "$CH_{30}OH$" should read --$CH_3OH$--

Col. 5, line 5. "inert solid" should read --'inert solid'--

Claim 1, line 4. "contaiing" should read --containing--

Claim 2, line 2. "amidiine" should read --amidine--

Claim 13, line 12 (last line). change comma after "hydrogen" to period
"hydrogen," should read --hydrogen.--

Claim 20, line 3. "R1" should read --$R^1$--

Claim 21, line 2. insert --silyl-- before the word "ether"

Claim 21, line 10. change "y = 0 to 3 pO P > 0" to read
--y = 0 to 3 P > 0--

Signed and Sealed this

Tenth Day of March, 1987

*Attest:*

DONALD J. QUIGG

*Attesting Officer*     *Commissioner of Patents and Trademarks*